US009489732B1

(12) United States Patent
Khosla et al.

(10) Patent No.: US 9,489,732 B1
(45) Date of Patent: Nov. 8, 2016

(54) VISUAL ATTENTION DISTRACTOR INSERTION FOR IMPROVED EEG RSVP TARGET STIMULI DETECTION

(71) Applicant: HRL Laboratories, LLC, Malibu, CA (US)

(72) Inventors: Deepak Khosla, Camarillo, CA (US); Kevin R. Martin, Oak Park, CA (US); David J. Huber, Calabasas, CA (US)

(73) Assignee: HRL Laboratories, LLC, Malibu, CA (US)

( * ) Notice: Subject to any disclaimer, the term of this patent is extended or adjusted under 35 U.S.C. 154(b) by 194 days.

(21) Appl. No.: 14/206,421

(22) Filed: Mar. 12, 2014

Related U.S. Application Data (63) Continuation-in-part of application No. 12/975,352, filed on Dec. 21, 2010, now Pat. No. 8,699,767.

(60) Provisional application No. 61/779,258, filed on Mar. 13, 2013.

(51) Int. Cl.
  *G06T 7/00* (2006.01)
  *G06K 9/00* (2006.01)

(52) U.S. Cl.
  CPC ......... *G06T 7/0012* (2013.01); *G06K 9/00496* (2013.01)

(58) Field of Classification Search
  None
  See application file for complete search history.

(56) References Cited

U.S. PATENT DOCUMENTS

| | | | |
|---|---|---|---|
| 6,670,963 B2 | 12/2003 | Osberger | |
| 6,925,455 B2 * | 8/2005 | Gong | G06F 17/30029 348/E7.063 |
| 7,835,581 B2 | 11/2010 | Mathan et al. | |
| 8,374,687 B2 | 2/2013 | Mathan et al. | |
| 8,483,816 B1 * | 7/2013 | Payton et al. | 600/544 |
| 9,224,044 B1 * | 12/2015 | Laska | H04N 5/2628 |
| 2005/0047647 A1 | 3/2005 | Rutishauser et al. | |
| 2006/0101079 A1 * | 5/2006 | Morikawa | A61B 5/04 |
| 2007/0173699 A1 | 7/2007 | Mathan et al. | |

(Continued)

FOREIGN PATENT DOCUMENTS

WO    WO 03/093947    11/2003

OTHER PUBLICATIONS

Sun, Y., et al., "Probabilistic judgment by a coarser scale: behavioral and ERP evidence," in Proceedings ref the Twenty-sixth Annual meeting of the Cognitive Science Society, 2004.

(Continued)

*Primary Examiner* — Michelle Entezari
(74) *Attorney, Agent, or Firm* — Tope-McKay & Associates (57) ABSTRACT

Described is a system for improved electroencephalograph (EEG) rapid serial visual presentation (RSVP) target stimuli detection through visual attention distractor insertion. A first RSVP sequence is created comprising a set of image chips. The image chips are a combination of target images containing target events and non-target images containing comment events. A number of visual attention distractors to optimize target event detection is determined, and the determined number of visual attention distractors is inserted into the first RSVP sequence to generate a second RSVP sequence. The second RSVP sequence is reordered to generate a third RSVP sequence. The third RSVP sequence is presented to a user, and an EEG signal is received from the user. Finally, the EEG signal is decoded to identify a true target event via a P300 detection in the EEG signal.

12 Claims, 6 Drawing Sheets

(56) References Cited

U.S. PATENT DOCUMENTS

| | | | |
|---|---|---|---|
| 2007/0236488 A1 | 10/2007 | Mathan et al. | |
| 2008/0056611 A1 | 3/2008 | Mathan et al. | |
| 2009/0312665 A1* | 12/2009 | Daimoto | A61B 5/0482 600/544 |
| 2012/0172743 A1* | 7/2012 | Aguilar et al. | 600/544 |

OTHER PUBLICATIONS

Thorpe, S., et al., "Speed of processing in the human visual system," Nature, vol. 381, pp. 520-522, 1996.
University of California, San Diego Complex Systems and Cognition Laboratory, CSCLAB Image Database http://csclab.ucsd.edu/labeledimages.php. 2006.
Walther D., et al, "Attentional selection for object recognition—a gentle way," Lecture Notes in Computer Science 2525: 472-479, 2002.
Wolfe J.M., "Visual Search in continuous, naturalistic stimuli," Vision Research 34: 1187-1195, 1994.
Vazirani, V., "Approximation Algorithms," Springer-Verlag, Berlin, Germany. pp. 32-33 (2004).
Vogel, E.K., et al., "The Visual N1 Component as an index of a discrimination process," Psychophysiology, 2000.
Yamaguchi, S., et al., "Cerebral Asymmetry of the 'Top-down' allocation of attention to global and local features," The Journal of Neuroscience, 20, 1-5, 2000.
Zang H., et al., "SVM-KNN: Discriminative nearest neighbor classification for visual category recognition," CVPR 2006.26.
Vazirani, V., "Approximation algorithms," Springer-Verlag, Berlin, Germany, p. 32, 2004.
http://en.wikipedia.org/Travelling_salesman_problem, Dec. 2, 2009.
Richard P. Wildes, "A measure motion salience for surveillance applications" in Proc. IEEE Int'l Conf. Image Processing,1998.
Andoni A., et al., "Near-Optimal Hashing Algorithms for Near Neighbor Problem in High Dimension," Proceedings of the Symposium on Foundations of Computer Science (FOCS'06), 2006.
Bentin, S., et al., "Electrophysiological studies of face perception in humans," Journal of Cognitive Neuroscience. 8, 551-565, 1996.
Berg A., "Shape matching and object recognition," Ph.D. thesis, UC Berkeley, Computer Science Division, Berkeley, CA, Dec. 2005.
Berke, C., et al., "Evaluation of an EEG-workload model in an aegis simulation environment" in Proceedings of SPIE Defense and Security Symposium, 90-99, 2005.
Bhattacharyya, R., et al., "Optimal image ordering for rapid serial visual presentation using electroencephalography," Presented at Society of NeuroScience (SfN) annual meeting, Chicago, 2009.
Carpenter G.A., et al., "A massively parallel architecture for a self-organizing neural pattern recognition machine," Computer Vision, Graphics, and Image Processing, 37, 54-115, 1987.
Carpenter G.A., et al., "The what-and-where filter a spatial mapping neural network for object recognition and image understanding," Computer Vision and Image Understanding. 69, 1-22, 1998.
Carpenter G.A., "Default ARTMAP," in Proc. of the International Joint Conference on Neural Networks (IJCNN'03), 1396-1401, 2003.
Carpenter G.A., et al., "Self-organizing information fusion and hierarchical knowledge discovery: a new framework using ARTMAP neural networks," Neural Networks, 18, 287-295, 2005.
Cowell, et al., "Construction and validation of neurophysio-technological framework for imagery analysis," in J.Jacke (Ed.): Human-Computer Interaction, Part II. HCII 2007, LNCS 4551, pp. 1096-1105, 2007, © Springer-Verlag Berlin Heidelberg.
Draper B., et al., "Evaluation of Selective Attention under Similarity Transforms," In Workshop on Performance and Attention in Computer Vision. Graz, Austria, Apr. 2003.
Eckhorn R., et al., "Coherent Oscillations. A Mechanism of feature linking in the visual cortex?" Biological Cybernetics 60, 121-130, 1988.
Elmer, M., "Does the face-specific N170 component reflect the activity of a specialized eye processor?" Neurererport, 9, 2945-2948, 1998.
Fabre-Thorpe, M., et al., "A limit to the speed of processing in Ultra-Rapid visual categorization of novel natural scenes," Journal of Cognitive Neuroscience, 13, 171-180, 2001.
Field D.J., "Relations between the statistics of natural images and the response properties of cortical cells," J. Opt. Soc. Am. A., 4: 2379-2394, 1987.
Fei-Fei L., et al., "Learning generative visual models from few training examples: an incremental Bayesian approach tested on 101 object categories," CVPR 2004, Workshop on Generative-Model Based Vision, 2004.
Gerson, A.D., et al., "Cortically coupled computer vision for rapid image search," IEEE Transactions on Neural Systems and Rehabilitation Engineering, 14(2): 174-179, Jun. 2006.
Gladwell M.; "Blink: the power of thinking without thinking," 1st ed. Little, brown and company: Time Warner Book Group, New York, 2005, pp. 18-47.
Gutin, G., et al., "Traveling salesman should not be greedy: domination of analysis of greedy-type heuristics for the TSP," Discrete Applied Mathematics, 117: 81-86, 2002.
Gray C.M., et al., "Oscillatory Responses in Cat visual cortex exhibit intercolumnar synchronization which reflects global stimulus properties," Nature 338: 334-336. 1989.
Hopf, J.-M., et al., "Localizing visual discrimination processes in time and space," The American Physiological Society, 88, 2088-2095, 2002.
Itti L., et al., "A saliency-based search mechanism for overt and covert shifts of visual attention," Vision Research, 40: 1489-1506, 2000.
Itti L., et al., "A Model of Saliency-Based Visual Attention for Rapid Scene Analysis," IEEE Transactions on Pattern Analysis and Machine Intelligence, 20, 1254-1259, 1998.
Itti L., et al., "Bayesian Surprise Attracts Human Attention," Vision Research 49: 1295-1306, 2008.
Itti, L., et al., "Computational Modeling of Visual Attention," Nature Reviews Neuroscience, 2, 194-203, 2001.
Itti, L., "Quantifying the Contribution of low-level saliency to human eye movements in dynamic scenes," Visual Cognition, 12, 1093-1123, 2005.
Keysers, C., et al., "The Speed of Sight," Journal of Cognitive Neuroscience, 13(1), 90-101, 2001.
Khosla D., et al., "Bio-Inspired Visual Attention and Object Recognition," In: Proc. SPIE Defense, Security, and Sensing, 6560, 656003, 2007.
Khosla, D., et al., "A bio-inspired system for spatio-temporal recognition in static and video imagery," Proc. SPIE 6560, 656002, 2007.
Koch C., et al., "Shifts in selective visual attention: towards the underlying neural circuitry," Human Neurobiology, 4: 219-227, 1985.
Lazebnik S., et al., "Beyond Bags of Features: spatial pyramid matching for recognizing natural scene categories," In: Proc. IEEE Conference on Computer Vision and Pattern Recognition (CVPR), 2006.
Ling, H., et al., "Diffusion distance for histogram comparison," IEEE Computer Society Conference on Computer Vision and Pattern Recognition (CVPR), 2006.
Medasani, S., et al., "Possibilistic particle swarms for optimization," Proceedings 5673 of SPIE/IST Symposium on Electronic Imaging, 2005.
Medasani, S., et al., "Active learning tem for object fingerprinting," International Joint Conference on Neural Networks, 2004.
Morrison, D., et al., "Semantic clustering of images using patterns of relevance feedback," in Proceedings of the 6th International Workshop on Content-based Multimedia Indexing (CBMI 2008), London, UK.
Nane S.A., et al., "Columbia Object Image Library (COIL-100)," Technical Report CUCS-006-96, Feb. 1996.
Navalpakkam V., et al., Modeling the influence of Task on Attention. Vision Research, 45: 205-231, 2005.

(56) References Cited

OTHER PUBLICATIONS

Navalpakkam V., et al., "An integrated model of top-down and bottom-up attention for optimal object detection," Proc. IEEE Conference on Computer Vision and Pattern Recognition (CVPR), 1-7, 2006.

Navalpakkam V., et al., "Sharing resources: buy attention, get recognition," In: Proc. International Workshop on Attention and Performance in Computer Vision (WAPCV'03), Graz, Austria, Jul. 2003.

Navalpakkam, V, et al., "Search goal tunes visual features optimally," Neuron, 53, 605-617, 2007.

Niebur E., at al., "Control of selective visual attention modeling the 'where' pathway," In D. Touretzky, M Mazer and M. Hasselmo. Neural Imformation Processing Systems (NIPS 8), 802-808, Cambridge, MA, MIT, Press 1996.

Orabona F., et al., "Object-based Visual Attention: A Model for a Behaving Robot," In 3rd International Workshop on Attention and Performance in Computational Vision (in CVPR 2005). San Diego, CA, Jun. 2005.

Owechko, Y., et al., "A swarm-based volition/attention framework for object recognition," IEEE Conference on Computer Vision and Pattern Recognition, San Diego, 2005.

Owechko, Y., et al., "Cognitive swarms for rapid detection of objects and associations in visual imagery," IEEE Swarm Intelligence Symposium, 2005.

Peters, R.J., et al, "Beyond bottom-up: Incorporating task-dependent influences into computational model of spatial attention," in: Proc. IEEE Conference on Computer Vision and Pattern Recognition (CVPR), 2007.

Rogowitz, B.E., et al., "Perceptual image similarity experiments," Proceedings of SPIE, 3299: 576-590, 1998.

Scholl B.J., "Objects and Attention: the state of the art," Cognition 80, 1-46 2001.

Serre T., et al., "Object recognition with features inspired by visual cortex," in Proceedings of the IEEE conference on computer vision and pattern recognition (CVPR), San Diego, CA, Jun. 2005.

Smeulders, A., et al., "Content-based image retrieval at the end of the early years," IEEE Transactions PAMI, 22 (12): 1349-1380, 2000.

Sun Y., et al., "Hierarthical selectivity for object-based visual attention," Submitted to Artificial Intelligence, 2004.

Rajah Bhattacharyya, Deepak Khosla, Davd Huber, Penn Tasinga, "Optimal Image Ordering for Rapid Serial Visual Presentation Using Electroencephalography," SfN NeuroScience 2009, Oct. 17-21, Chicago, Postere Presentation, (2009).

Deepak Khosla, David J. Huber, Rajan Bhattacharyya, Mike Daily, Penn Tasinga, "Neurally Inspired Rapid Detection of Sparse Objects in videos," Signal Processing, Sensor Fusion, and Target Recognition XIX, Proc. of SPIE vol. 7697, 76971C, (2010).

Steven B. Most. Marvin M. Chun, David M. Widders and David H. Zald, "Attentional rubbernecking: Cognitive control and personality in emotion-induced blindness", Psychonomic Bulletin & Review, (2005) vol. 12, No. 4, 654-651 DOI: 10.3758/BF03196754.

Bernhard Hommel and Eikan C. Akyüre; Lag-1 sparing in the attentional blink:Benefits and costs of integrating two events into a single episode. The Quarterly Journal of Experimental Psychology (2005), 58A (8), 1415-143.

Nieuwenhuis S. Gilzenrat MS, Holmes BD, Cohen JD (Aug. 2005). "The role of the locus coerleus in mediating the attentional blink: a neurocomputational theory". J Exp Psychol Gen 134 (3): 291-307. doi:10.1037/0096-3445.134.3.291. PMID 16131265.

Thorpe, et al., "Speed of Processing in the Human Visual System", Nature, vol. 381, pp. 520-522, 1996.

Khosla, et al., "Optimal detection of objects in images and videos using elecroencephalography (EEG)," Proc. SPIE 8050, Signal Processing, Sensor Fusion, and Target Recognition XX, edited by Ivan Kadar, Proc. of SPIE vol. 8050 (May 4, 2011).

Raymond, et al., "Temporary suppression of visual processing in an RSVP task: an attentional blink?" Journal of experimental psychology. Human perception and performance 18 (3): pp. 849-860, 1992.

\* cited by examiner

VISUAL ATTENTION DISTRACTOR INSERTION FOR IMPROVED EEG RSVP TARGET STIMULI DETECTION

CROSS-REFERENCE TO RELATED APPLICATIONS

This is a Continuation-in-Part application of U.S. Non-Provisional application Ser. No. 12/975,352, filed in the United States on Dec. 21, 2010, entitled, "System for Optimal Rapid Serial Visual Presentation (RSVP) from User-Specific Neural Brain Signals."

This is ALSO a Non-Provisional patent application of U.S. Provisional Application No. 61/779,258, filed in the United States on Mar. 13, 2013, entitled, "Vision Attention Distractor Insertion for Improved EEG RSVP Target Stimuli Detection."

GOVERNMENT LICENSE RIGHTS

This invention was made with government support under U.S. Government Contract Number W31P4Q-08-C-0264 CT2WS. The government has certain rights in the invention.

BACKGROUND OF THE INVENTION (1) Field of Invention

The present invention relates to a system for improved electroencephalography (EEG) rapid serial visual presentation (RSVP) stimuli detection and, more particularly, to a system for improved EEG RSVP stimuli detection through insertion of visual attention distracters.

(2) Description of Related Art

Rapid serial visual presentation (RSVP) measures the brain activity of a human subject while watching a stream of rapid images in order to find incongruities and inconsistencies in the images (i.e., "targets"). It is well known, though not completely understood, that humans experience both attentional blink and repetition blindness when searching for objects of interest (i.e., targets) in a target rich RSVP. Prior art related to RSVP-based attentional blink and repetition blindness have focused on understanding the underlying visual and cognitive causes. In some cases attentional blink has been theorized to be caused by conceptual similarities and in other cases by emotional mediated attention, as described by Most et al. in "Attentional Rubbernecking: Cognitive control and personality in emotion-induced blindness", Psychonomic Bulletin & Review, Volume 12, Number 4, 654-661.

Still furthering the confusion at understanding attentional blink has been the effect of "Lag 1" sparing. When two rapidly presented targets (T1 and T2) occur within about a halfa second of each other, T2 is often missed. However, if T2 immediately follows T1, performance is often reported being as good as that at long lags, as described by Hommel and Akyüre in "Lag-1 Sparing in the Attentional Blink: Benefits and Costs of Integrating Two Events into a Single Episode", The Quarterly Journal of Experimental Psychology 2005, 58A (8), 1415-143. One hypothesis to explain the Lag 1 sparing involves the release of a neurotransmitter that benefits the detection of the stimulus for 100 milliseconds before the neurons in the locus coeruleus enter a refractory period, due to the auto-inhibitory effect of the neurotransmitter norepinephrine, as described by Nieuwenhuis et al. in "The Role of the Locus Coeruleus in Mediating the Attentional Blink: a Neurocomputational Theory", Journal of Experimental Psychology: General 134 (3): 291-307, 2005.

While the causes of these phenomenon are being researched and debated, no known attempts have been made to utilize the empirical results to develop a method to improve EEG based threat detection in a target rich RSVP sequence. Thus, a continuing need exists for a method that utilizes the empirical results to determine improvements to RSVP sequences.

SUMMARY OF THE INVENTION

The present invention relates to a system for improved electroencephalography (EEG) rapid serial visual presentation (RSVP) stimuli detection and, more particularly, to a system for improved EEG RSVP stimuli detection through insertion of visual attention distracters. The system comprises one or more processors and a memory having instructions such that when the instructions are executed, the one or more processors perform multiple operations. creating a first RSVP sequence, wherein the first RSVP sequence comprises a set of image chips. The set of image chips comprises a combination of target images containing at least one target event and non-target images containing common events. The system determines a number of visual attention distractors to optimize target event detection. The determined number of visual attention distractors is then inserted into the first RSVP sequence to generate a second RSVP sequence. The second RSVP sequence is reordered to generate a third RSVP sequence. Next, the third RSVP sequence is presented to a user, and an EEG signal is received from the user. Finally, the EEG signal is decoded to identify a true target event via a P300 detection in the EEG signal.

In another aspect, the number of visual attention distractors is determined based on establishing an optimal ratio of a probability of target events to common events for a maximum P300 detection in the EEG signal.

In another aspect, the number of visual attention distractors, K, is determined according to the following:

$$K=[(R_E/R_I)-1]*N \text{ if } R_E>R_I; =0 \text{ otherwise,}$$

where N denotes a number of image chips in the first RSVP sequence, E represents a number of expected target events in the first RSVP sequence; P denotes a probability of detection of a target event in the first RSVP sequence by a cognitive algorithm, $R_I$ represents an ideal ratio of target events to common events for a maximum P300 detection in the EEG signal, and an expected ratio of target events to common events, $R_E$, is equal to $(P*E)/N$.

In another aspect, the visual attention distractors are visually similar to the non-target images containing common events obtained during creation of the first RSVP sequence.

In another aspect, reordering the second RSVP sequence maximizes a likelihood of detecting a true target event and minimizes a likelihood of detecting false alarms.

In another aspect, the present invention also comprises a method for causing a processor to perform the operations described herein.

Finally, in yet another aspect, the present invention also comprises a computer program product comprising computer-readable instructions stored on a non-transitory computer-readable medium that are executable by a computer having a processor for causing the processor to perform the operations described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a system for improved electroencephalography (EEG) rapid serial visual presentation (RSVP) stimuli detection and, more particularly, to a system for improved EEG RSVP stimuli detection through insertion of visual attention distracters. The following description is presented to enable one of ordinary skill in the art to make and use the invention and to incorporate it in the context of particular applications. Various modifications, as well as a variety of uses, in different applications will be readily apparent to those skilled in the art, and the general principles defined herein may be applied to a wide range of embodiments. Thus, the present invention is not intended to be limited to the embodiments presented, but is to be accorded with the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter-clockwise have been used for convenience purposes only and are not intended to imply any particular fixed direction. Instead, they are used to reflect relative locations and/or directions between various portions of an object. As such, as the present invention is changed, the above labels may change their orientation.

(1) Principal Aspects

The present invention has three "principal" aspects. The first is a system for improved electroencephalography (EEG) rapid serial visual presentation (RSVP) stimuli detection. The system is typically in the form of a computer system, computer component, or computer network operating software or in the form of a "hard-coded" instruction set. This system may take a variety of forms with a variety of hardware devices and may include computer networks, handheld computing devices, cellular networks, satellite networks, and other communication devices. As can be appreciated by one skilled in the art, this system may be incorporated into a wide variety of devices that provide different functionalities. The second principal aspect is a method for improved EEG RSVP stimuli detection. The third principal aspect is a computer program product. The computer program product generally represents computer-readable instruction means (instructions) stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories.

The term "instructions" as used with respect to this invention generally indicates a set of operations to be performed on a computer, and may represent pieces of a whole program or individual, separable, software modules. Non-limiting examples of "instructions" include computer program code (source or object code) and "hard-coded" electronics (i.e., computer operations coded into a computer chip). The "instructions" may be stored on any non-transitory computer-readable medium such as a floppy disk, a CD-ROM, a flash drive, and in the memory of a computer.

(2) Specific Details

Most imagery is visually analyzed by humans to search for "Objects of Interest" (OI) (e.g., targets and suspicious activity in videos from wide field-of-view sensors, unmanned aerial vehicle (UAV) drones, satellite imagery). This work is manual, slow, and could miss objects of interest. A large volume of imagery is also never looked at because of human analyst resource shortage.

To overcome these limitations, there has been a surge of interest in developing and using automated computer algorithms and software to aid and/or emulate human visual perception in imagery analysis, present likely targets to a human operator by using rapid serial visual presentation (RSVP), and decode the human's electroencephalogram (EEG) signal to identify targets via the P300 response.

Various RSVP image ordering processes for rapid threat search and detection were described in U.S. Pat. No. 8,285,052, entitled, "Image Ordering System Optimized via User Feedback" (hereinafter referred to as the '052 patent) and U.S. application Ser. No. 12/975,352, entitled, "System for Optimal Rapid Serial Visual Presentation (RSVP) from User-Specific Neural Brain Signals," (hereinafter referred to as the '352 application), both of which are hereby incorporated by reference as though fully set forth herein. It is well known, though not completely understood, that humans experience both attentional blink and repetition blindness when searching for OIs in a target rich RSVP. Most work in the area of attentional blink and repetition blindness has been focused on understanding the underlying causes rather than taking advantage of the known effects to insert distractors to optimize detection.

(2.1) Experimental Studies

A set of RSVP EEG experiments were conducted and results were obtained which support the theory behind the method for distractor insertion according to the principles of the present invention. The goal of these experiments was to determine the target load at which threat detection performance degrades. One source of error in this task is a phenomenon known as attentional blink, the unawareness of target stimuli occurring directly, or soon after, an earlier target stimulus.

Another source of error is a phenomenon known as repetition blindness, which is the lower likelihood of detecting the repetition of a similar target soon after an earlier target stimulus. The dataset used in the experiments described below allowed for errors associated with attentional blink and repetition blindness. The experiments also allowed for errors that may be caused by other factors not related to these phenomenons, such as exceptionally small targets, low saliency, low contrast targets, and non-moving targets. It was hypothesized that as the number of targets in a given selection of video RSVP clips goes up, the probability of detecting targets would go down, and participants would admit more false positives.

In the experiment, subjects were asked to press a button each time they saw a vehicle or human in a collection of RSVP sequences while wearing an EEG headset. The number of targets per RSVP sequence was varied. All sequences were comprised of fifty five-frame video clips, totaling 250 images per RSVP block.

The number of targets per RSVP sequence was varied within-subjects at levels of three, five, and seven targets per RSVP sequence. The remaining video clips in each block were distractors containing no targets. Twenty-five sequences were presented for each condition. The component video clips in each sequence contained scenes of empty desert, vehicles, or people walking. Vehicles and people walking were designated as targets (i.e. the rare events); all other content was considered non-target distractors.

Sequences were displayed as a 512 pixels square against a 50% gray background on a display monitor. Participants were positioned approximately 25 inches away from the display monitor in a quiet room and closely surrounded by a drape to limit external distractions. EEG data was collected using a 20 channel Advanced Brain Monitoring (ABM) ×24 SDK EEG headset, and timing information was fed in using ABM's External Sync Unit (ESU). ABM is located at 2237 Faraday Ave., Suite 100, Carlsbad, Calif., 92008. The experimental software used to display sequences and read in EEG data was programmed in-house using C++, OpenCV, and ABM's software SDK. An XBox controller (Microsoft, Redmond, Wash.) was integrated into this software and used to collect participant feedback.

First, the ABM headset was set up and adjusted according to an impedance check. Participants were then instructed on the task as follows. While wearing the ABM EEG headset, the participants were to view the video and/or image sequences, and press a button on their XBox controller each time they saw a walking figure or a vehicle. They were told to relax and were discouraged from blinking, making sudden movements, and clenching their jaws while viewing the sequences. A red dot was displayed between each sequence. At this point, participants were instructed to take breaks if necessary, or indicate if they were ready to see the next sequence by pressing a button on the XBox controller.

Each sequence was comprised of 50 video clips or still images with one target stimulus and 49 non-target stimuli in each. For both the still image and video sequence type conditions participants were exposed to a set of 50 sequences and then a set of 25 sequences. The order of the sequences within each set was randomized, and the order of presentation of the conditions was varied between subjects to control for ordering effects. Once the data was collected, a P300 target detection classifier was trained on EEG and ground truth data from the sets of 50 sequences and tested on the EEG data from the sets of 25.

Figure 1:
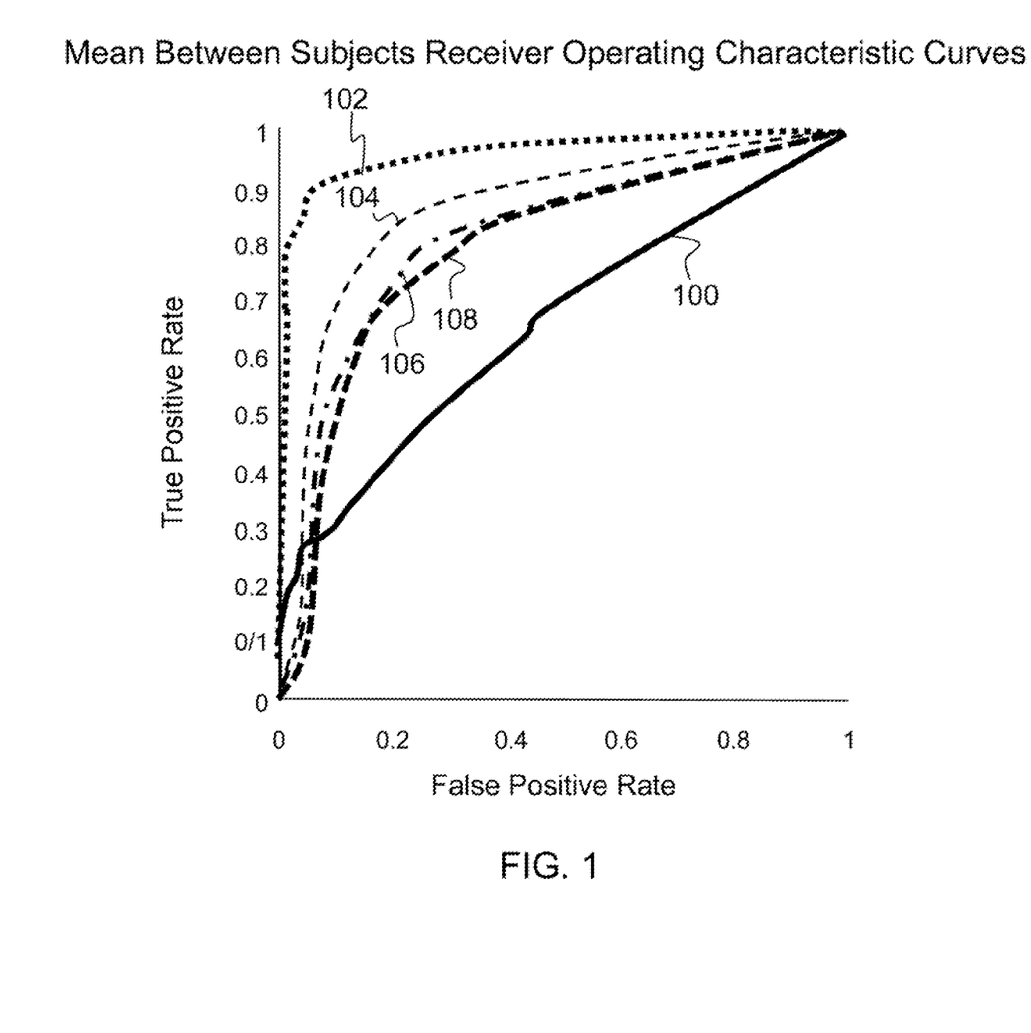
FIG. 1 is a receiver operating characteristic (ROC) plot of rapid serial visual presentation (RSVP) threat detection performance for various threat counts according to the principles of the present invention.

FIG. 1 illustrates a receiver operating characteristic (ROC) plot of RSVP threat detection performance for various threat (target stimulus) counts. Along the x-axis is the false positive rate, and along the y-axis is the true positive rate. Curve 100 represents one target stimulus in a static image, curve 102 represents one target stimulus in a video, curve 104 represents three target stimuli in a video, curve 106 represents five target stimuli in a video, and curve 108 represents seven target stimuli in a video.

As the number of targets in each sequence increased, A' consistently decreased and the number of false positives consistently increased. For the three (represented by curve 104), five (represented by curve 106), and seven (represented by curve 108) target videos, a three group one-way analysis of variance showed that no group was significantly different than any of the others $F(1,7)=0.45$, $p=0.65$. Trends towards decreasing A' and increasing false positives were observed. A' is traditional shorthand for Area Under the Curve (AUC). AUC has an important statistical property for target discrimination: the AUC of a classifier is equivalent to the probability that the classifier will rank a randomly chosen positive instance higher than a randomly chosen negative instance. An AUC of 0.5 is basically equivalent to a random guess (e.g., a coin toss) and, therefore, worthless. Higher AUCs are better, with an AUC of 1.0 representing a perfect classifier.

Figure 2A:
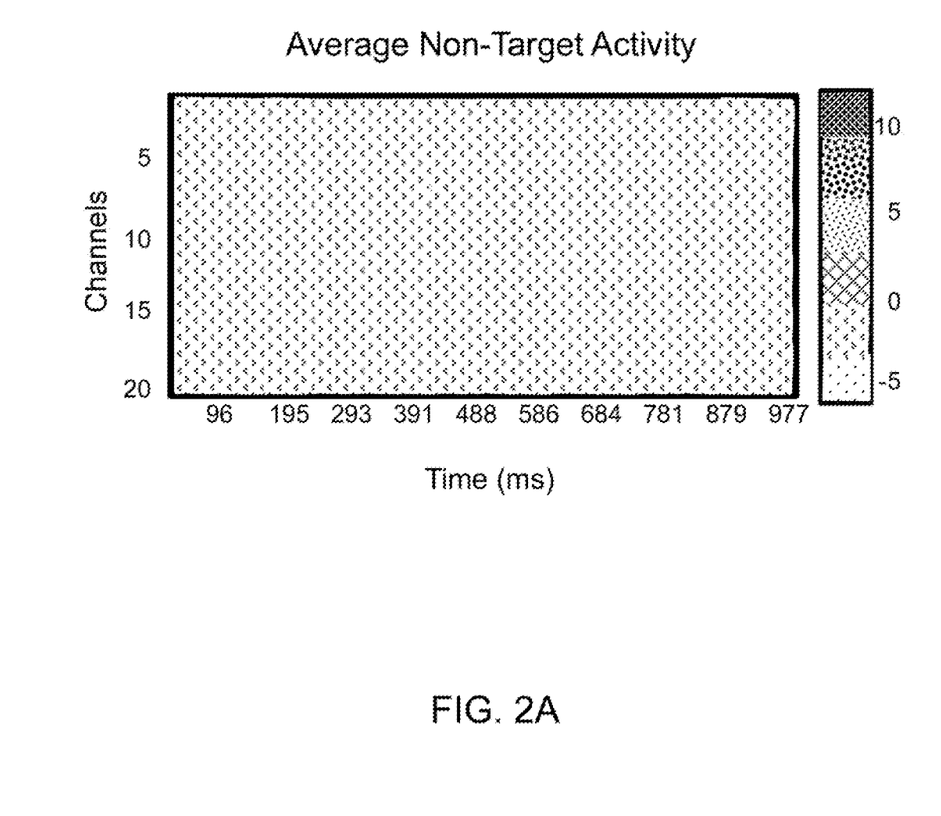
FIG. 2A is an average electroencephalography (EEG) response plot for non-target activity according to the principles of the present invention.
Figure 2B:
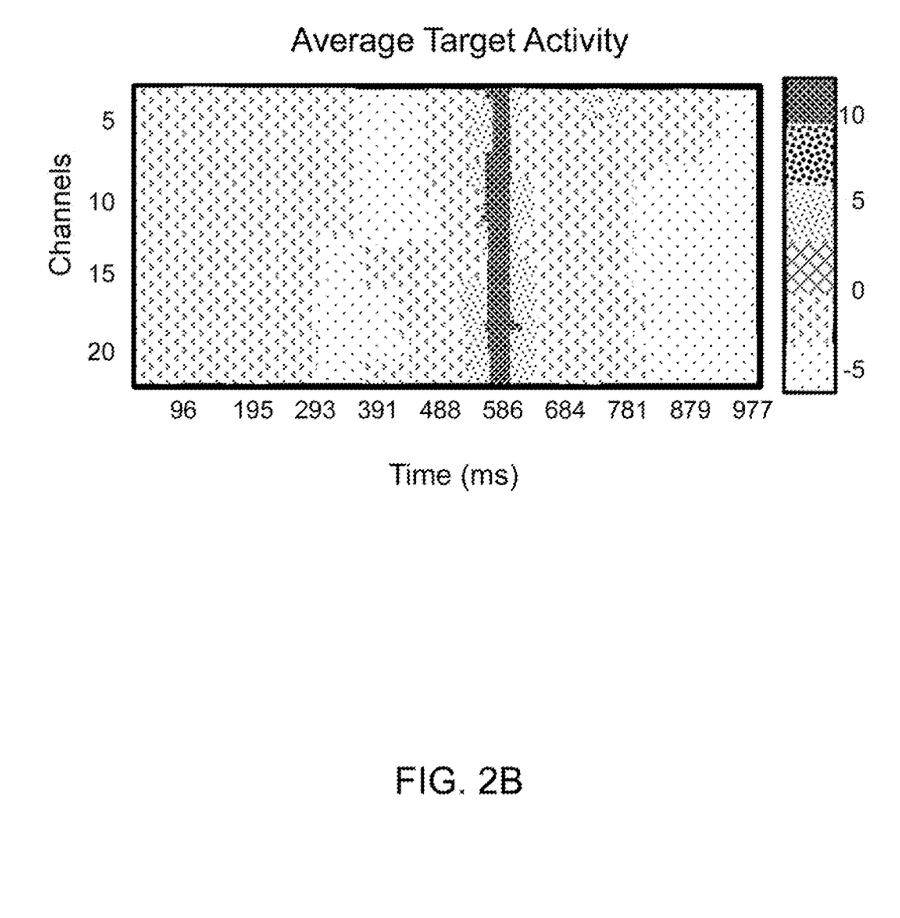
FIG. 2B is an average EEG response plot for target activity according to the principles of the present invention.

FIGS. 2A and 2B depict response plots of the EEG activity on the scalp of a single participant without and with a target present in the RSVP stream, respectively. The plot in FIG. 2A shows average activity when no target is present. The plot in FIG. 2B shows average activity during the presence of a target. P300 activity is evident at approximately 400 milliseconds in the form of a large positive flux in the parietal and occipital lobes. The large positive flux is indicated by the change from −5 to 0, and eventually 5 to 10 in response intensity. The channel numbers along the x-axis refer to different areas of the brain that are measured by the system, such as the parietal and occipital lobes.

(2.2) Optimal Insertion of Distractors

The experiment results indicated that the best performance under these experimental conditions was obtained when there was one threat clip (i.e., a "rare" event) amongst the fifty events (of which the other forty-nine were common distractor events), as indicated by curve 102 in FIG. 1. The distractor insertion process according to the principles of the present invention maintains this low rare event/common event ratio even in high threat (target) environments by inserting additional common distractor clips to artificially enable the performance improving ratio. By inserting these additional distractors, the operator is less likely to experience the effects of attentional blink and repetition blindness, and the resulting EEG signal will present stronger correlations with the desired P300 signal to indicate each threat that was detected.

The process to determine the number of distractors for a given image RSVP sequence is given as follows:

Number of distractors to insert, $K_i = [(R_E/R_I) - 1] * N$ if $R_E > R_I$; =0 otherwise, where N denotes the number of chips in the RSVP sequence (block), E represents the number of expected "rare" events in the environment (per block), P denotes the probability of detection by a front-end cognitive algorithm, $R_I$ represents an ideal ratio of rare events/common events for maximum P300 detection (typical R is 0.02), and the expected ratio of rare events/common events $R_E = (P*E)/N$ The following is an example of distractor determination:

$N=50$, $E=10$, $P=0.5$, $R_I=0.02$;

$R_E=(0.5*10)/50=0.1$;

$K=(0.1/0.02-1)*(50)=200$ distractors need to be inserted.

In the above example, randomly inserting 200 distractors in the RSVP sequence will bring the rare/common ratio to an experimentally proven beneficial level, and improve the probability of detecting true positives in the EEG signal while simultaneously reducing the probability of false positives. Note that these distractors are usually randomly sampled from the same wide area scene for which the RSVP sequence is composed. Examples of RSVP sequences are described in further detail in the '052 patent and the '352 application.

(2.3) Reorder Sequence

The '052 patent and the '352 application describe algorithms for ordering chips in RSVP sequences to maximize the likelihood of true "target" detection while simultaneously minimizing the likelihood of false alarms and unintended subject response. In the reorder sequence step according to the principles of the present invention, the RSVP sequence from the distractor insertion process is reordered. The method of reordering is described in the '052 patent. This results in a newly re-ordered RSVP sequence which is presented to the user, and the EEG is then decoded in real-time to determine threat (OI) probabilities. Decoding of the EEG is described in U.S. Pat. No. 8,214,308, entitled, "Cognitive-Neural Method for Image Analysis" (hereinafter referred to as the '308 patent), which is hereby incorporated by reference as though fully set forth herein.

This invention described herein is useful for any application that employs the RSVP paradigm for rapid object detection and classification. For example, it can be employed in human-assisted threat assessment and threat queuing applications in which the system must scan a wide field-of-view and report any anomalies to the landscape. In these instances, automated classification methods might fail. Other examples of potential applications include automotive safety, factory safety and efficiency (e.g., sorting tasks), intelligence analysis, and surveillance.

Figure 3:
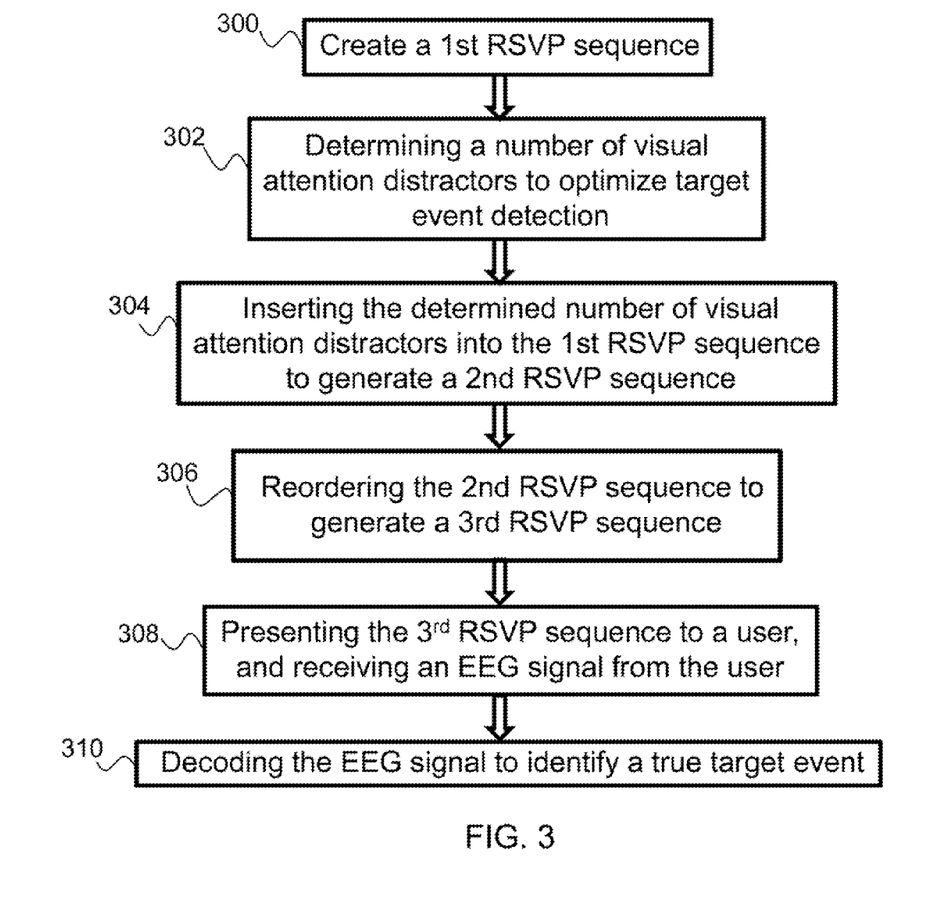
FIG. 3 is a flow diagram depicting a method for visual attention distractor insertion for improved EEG RSVP target stimuli detection according to the principles of the present invention.

FIG. 3 is a flow diagram depicting the method for visual attention distractor insertion and reordering for improved EEG RSVP target stimuli detection according to the principles of the present invention. As described above, in a first step 300 of the process, a first RSVP sequence is created. The RSVP sequences comprises a set of image chips which are a combination of target images containing at least one target event and non-target images containing common events. In a second step 302, a number of visual attention distractors to optimize target event detection is determined. In a third step 304, the determined number of visual attention distractors is inserted into the first RSVP sequence to generate a second RSVP sequence. In a fourth step 306, the second RSVP sequence is reordered to generate a third RSVP sequence. In a fifth step 308, the third RSVP sequence is presented to a user and an EEG signal is received from the user. Finally, in a sixth step 310 of the process, the EEG signal is decoded to identify a true target event via a P300 detection in the EEG signal.

Figure 4:
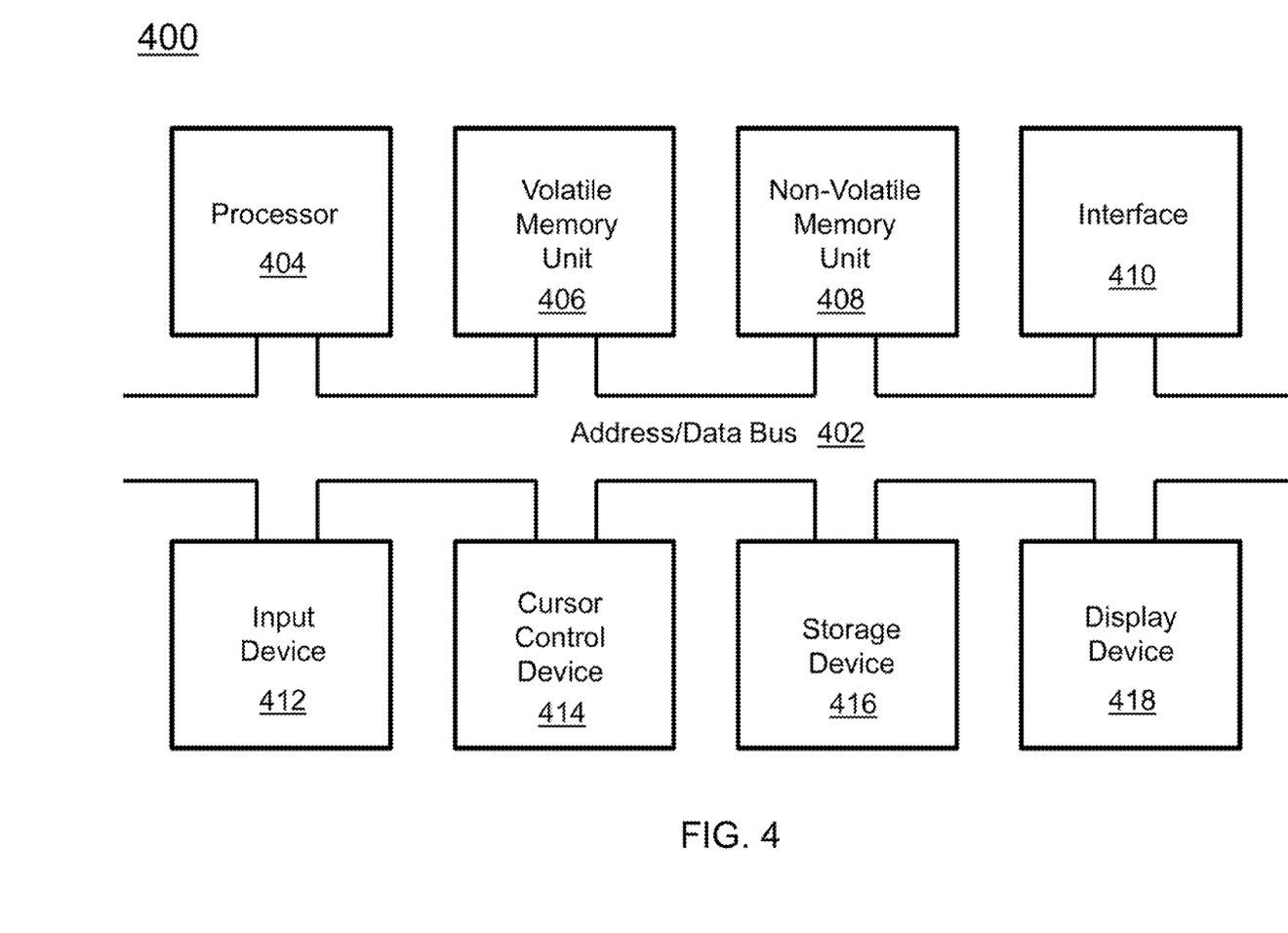
FIG. 4 is an illustration of a data processing system according to the principles of the present invention.

An example of a computer system 400 in accordance with one aspect is shown in FIG. 4. The computer system 400 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 400. When executed, the instructions cause the computer system 400 to perform specific actions and exhibit specific behavior, such as described herein.

The computer system 400 may include an address/data bus 402 that is configured to communicate information. Additionally, one or more data processing units, such as a processor 404, are coupled with the address/data bus 402. The processor 404 is configured to process information and instructions. In one aspect, the processor 404 is a microprocessor. Alternatively, the processor 404 may be a different type of processor such as a parallel processor, or a field programmable gate array.

The computer system 400 is configured to utilize one or more data storage units. The computer system 400 may include a volatile memory unit 406 (e.g., random access memory ("RAM"), static RAM, dynamic RAM, etc.) coupled with the address/data bus 402, wherein a volatile memory unit 406 is configured to store information and instructions for the processor 404. The computer system 400 further may include a non-volatile memory unit 408 (e.g., read-only memory ("ROM"), programmable ROM ("PROM"), erasable programmable ROM ("EPROM"), electrically erasable programmable ROM "EEPROM"), flash memory, etc.) coupled with the address/data bus 402, wherein the non-volatile memory unit 408 is configured to store static information and instructions for the processor 404. Alternatively, the computer system 400 may execute instructions retrieved from an online data storage unit such as in "Cloud" computing. In an embodiment, the computer system 400 also may include one or more interfaces, such as an interface 410, coupled with the address/data bus 402. The one or more interfaces are configured to enable the computer system 400 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 400 may include an input device 412 coupled with the address/data bus 402, wherein the input device 412 is configured to communicate information and command selections to the processor 400. In accordance with one aspect, the input device 412 is an alphanumeric input device, such as a keyboard, that may include alphanumeric and/or function keys. Alternatively, the input device 412 may be an input device other than an alphanumeric input device. In one aspect, the computer system 400 may include a cursor control device 414 coupled with the address/data bus 402, wherein the cursor control device 414 is configured to communicate user input information and/or command selections to the processor 400. In one aspect, the cursor control device 414 is implemented using a device such as a mouse, a track-ball, a track-pad, an optical tracking device, or a touch screen. The foregoing notwithstanding, in one aspect, the cursor control device 414 is directed and/or activated via input from the input device 412, such as in response to the use of special keys and key sequence commands associated with the input device 412. In an alternative aspect, the cursor control device 414 is configured to be directed or guided by voice commands.

In one aspect, the computer system 400 further may include one or more optional computer usable data storage devices, such as a storage device 416, coupled with the address/data bus 402. The storage device 416 is configured to store information and/or computer executable instructions. In one aspect, the storage device 416 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 418 is coupled with the address/data bus 402, wherein the display device 418 is configured to display video and/or graphics. In one aspect, the display device 418 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 400 presented herein is an example computing environment in accordance with one aspect. However, the non-limiting example of the computer system 400 is not strictly limited to being a computer system. For example, one aspect provides that the computer system 400 represents a type of data processing analysis that may be used in accordance with various aspects described herein. Moreover, other computing systems may also be implemented. Indeed, the spirit and scope of the present technology is not limited to any single data processing environment. Thus, in one aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, one aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 5:
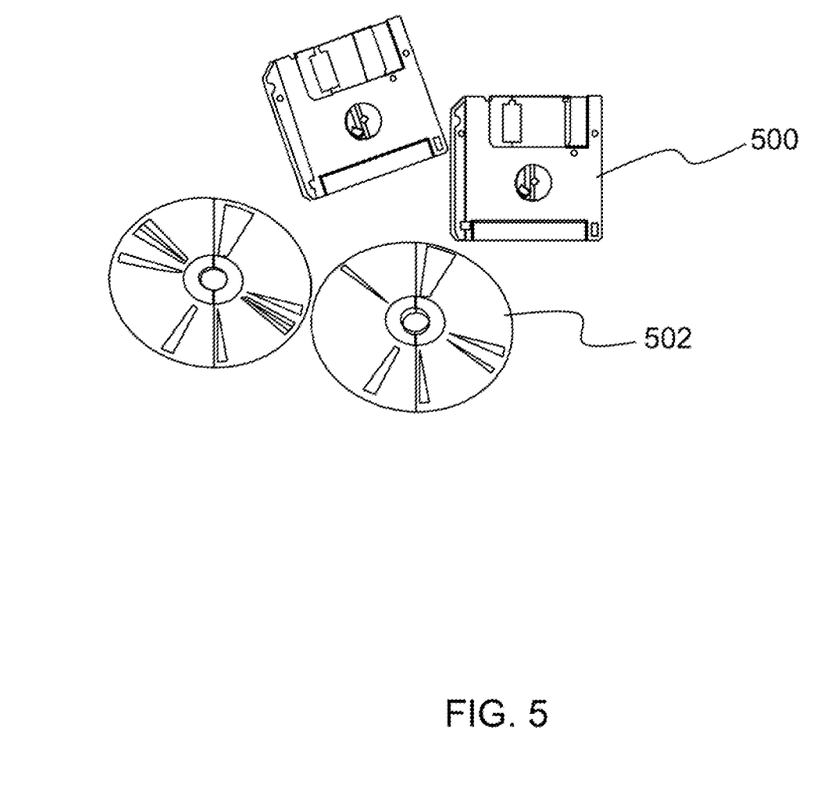
FIG. 5 is an illustration of a computer program product according to the principles of the present invention.

An illustrative diagram of a computer program product embodying the present invention is depicted in FIG. 5. As a non-limiting example, the computer program product is depicted as either a floppy disk 500 or an optical disk 502. However, as mentioned previously, the computer program product generally represents computer readable code (i.e., instruction means or instructions) stored on any compatible non-transitory computer readable medium.

What is claimed is:

1. A system for improved target stimuli detection, the system comprising:
   one or more processors and a non-transitory computer-readable medium having executable instructions encoded thereon such that when executed, the one or more processors perform operations of:
      creating a first rapid serial visual presentation (RSVP) sequence, wherein the first RSVP sequence comprises a set of image chips, wherein the set of image chips comprises a combination of target images containing at least one target event and non-target images containing common events;
      determining a number of visual attention distractors to optimize target event detection;
      wherein the visual attention distractors are visually similar to the non-target images containing common events obtained during creation of the first RSVP sequence;
      inserting the determined number of visual attention distractors into the first RSVP sequence to generate a second RSVP sequence;
      reordering the second RSVP sequence to generate a third RSVP sequence;
      presenting the third RSVP sequence to a user and receiving an electroencephalograph (EEG) signal from the user; and
      decoding the EEG signal to identify a true target event via a P300 detection in the EEG signal.

2. The system as set forth in claim 1, wherein determining the number of visual attention distractors is based on establishing an optimal ratio of a probability of target events to common events for a maximum P300 detection in the EEG signal.

3. The system as set forth in claim 2, wherein the number of visual attention distractors, K, is determined according to the following:

$$K=[(R_E/R_I)-1]*N \text{ if } R_E>R_I; =0 \text{ otherwise,}$$

where N denotes a number of image chips in the first RSVP sequence, E represents a number of expected target events in the first RSVP sequence; P denotes a probability of detection of a target event in the first RSVP sequence by a cognitive algorithm, $R_I$ represents an ideal ratio of target events to common events for a maximum P300 detection in the EEG signal, and an expected ratio of target events to common events, $R_E$, is equal to (P*E)/N.

4. The system as set forth in claim 3, wherein reordering the second RSVP sequence maximizes a likelihood of detecting a true target event and minimizes a likelihood of detecting false alarms.

5. A computer-implemented method for improved target stimuli detection, comprising an act of:
   causing one or more processors to execute instructions stored on a non-transitory memory such that upon execution, the data processor performs operations of:
      creating a first rapid serial visual presentation (RSVP) sequence, wherein the first RSVP sequence comprises a set of image chips, wherein the set of image chips comprises a combination of target images containing at least one target event and non-target images containing common events;
      determining a number of visual attention distractors to optimize target event detection;
      wherein the visual attention distractors are visually similar to the non-target images containing common events obtained during creation of the first RSVP sequence;
      inserting the determined number of visual attention distractors into the first RSVP sequence to generate a second RSVP sequence;
      reordering the second RSVP sequence to generate a third RSVP sequence;

presenting the third RSVP sequence to a user and receiving an electroencephalograph (EEG) signal from the user; and decoding the EEG signal to identify a true target event via a P300 detection in the EEG signal.

6. The method as set forth in claim 5, wherein determining the number of visual attention distractors is based on establishing an optimal ratio of a probability of target events to common events for a maximum P300 detection in the EEG signal.

7. The method as set forth in claim 6, wherein the number of visual attention distractors, K, is determined according to the following:

$$K=[(R_E/R_I)-1]*N \text{ if } R_E>R_I; =0 \text{ otherwise,}$$

where N denotes a number of image chips in the first RSVP sequence, E represents a number of expected target events in the first RSVP sequence; P denotes a probability of detection of a target event in the first RSVP sequence by a cognitive algorithm, $R_I$ represents an ideal ratio of target events to common events for a maximum P300 detection in the EEG signal, and an expected ratio of target events to common events, $R_E$, is equal to (P*E)/N.

8. The method as set forth in claim 7, wherein reordering the second RSVP sequence maximizes a likelihood of detecting a true target event and minimizes a likelihood of detecting false alarms.

9. A computer program product for improved target stimuli detection, the computer program product comprising computer-readable instructions stored on a non-transitory computer-readable medium that are executable by a computer having a processor for causing the processor to perform operations of:

creating a first rapid serial visual presentation (RSVP) sequence, wherein the first RSVP sequence comprises a set of image chips, wherein the set of image chips comprises a combination of target images containing at least one target event and non-target images containing common events;

determining a number of visual attention distractors to optimize target event detection;

wherein the visual attention distractors are visually similar to the non-target images containing common events obtained during creation of the first RSVP sequence;

inserting the determined number of visual attention distractors into the first RSVP sequence to generate a second RSVP sequence;

reordering the second RSVP sequence to generate a third RSVP sequence;

presenting the third RSVP sequence to a user and receiving an electroencephalograph (EEG) signal from the user; and decoding the EEG signal to identify a true target event via a P300 detection in the EEG signal.

10. The computer program product as set forth in claim 9, wherein determining the number of visual attention distractors is based on establishing an optimal ratio of a probability of target events to common events for a maximum P300 detection in the EEG signal.

11. The computer program product as set forth in claim 10, wherein the number of visual attention distractors, K, is determined according to the following:

$$K=[(R_E/R_I)-1]*N \text{ if } R_E>R_I; =0 \text{ otherwise,}$$

where N denotes a number of image chips in the first RSVP sequence, E represents a number of expected target events in the first RSVP sequence; P denotes a probability of detection of a target event in the first RSVP sequence by a cognitive algorithm, $R_I$ represents an ideal ratio of target events to common events for a maximum P300 detection in the EEG signal, and an expected ratio of target events to common events, $R_E$, is equal to (P*E)/N.

12. The computer program product as set forth in claim 11, wherein reordering the second RSVP sequence maximizes a likelihood of detecting a true target event and minimizes a likelihood of detecting false alarms.

\* \* \* \* \*